United States Patent
Spencer

[11] Patent Number: 6,132,833
[45] Date of Patent: *Oct. 17, 2000

[54] WAFER FOR USE IN SELECTIVE CONNECTING AND DISCONNECTING OF PLASTIC TUBES

[75] Inventor: Dudley W. C. Spencer, Wilmington, Del.

[73] Assignee: Denco, Wilmington, Del.

[ * ] Notice: This patent is subject to a terminal disclaimer.

[21] Appl. No.: 09/287,079

[22] Filed: Apr. 6, 1999

[51] Int. Cl.⁷ ...................................................... B32B 3/10
[52] U.S. Cl. .......................................... 428/64.1; 428/138
[58] Field of Search ................... 428/66.6, 64.1, 428/138; 156/503, 158

[56] References Cited

U.S. PATENT DOCUMENTS

| | | |
|---|---|---|
| 4,279,685 | 7/1981 | Barnett et al. . |
| 5,141,592 | 8/1992 | Shaposka et al. . |
| 5,156,701 | 10/1992 | Spencer et al. . |
| 5,158,630 | 10/1992 | Shaposka et al. . |
| 5,209,800 | 5/1993 | Spencer et al. . |
| 5,279,685 | 1/1994 | Ivansons et al. .......................... 156/158 |
| 5,397,425 | 3/1995 | Ivansons et al. . |
| 5,525,186 | 6/1996 | Ivansons et al. .......................... 156/503 |
| 5,632,852 | 5/1997 | Ivansons et al. . |
| 5,871,612 | 2/1999 | Spencer ................................... 156/503 |

*Primary Examiner*—Alexander S. Thomas
*Attorney, Agent, or Firm*—Connolly Bove Lodge & Hutz llp

[57] ABSTRACT

A wafer for use in the selective connecting and disconnecting of plastic tubes incorporates a fuse in an aperture. The fuse is made of a three layer laminate having light transmission characteristics which change after the wafer and its laminate have been heated. The three layers comprise two outer transparent layers and an intermediate layer having limited light transmission characteristics. When the wafer is heated the intermediate layer shrinks thereby changing the light transmission characteristics by providing a path for light to pass through the laminate without passing through the intermediate layer.

13 Claims, 1 Drawing Sheet

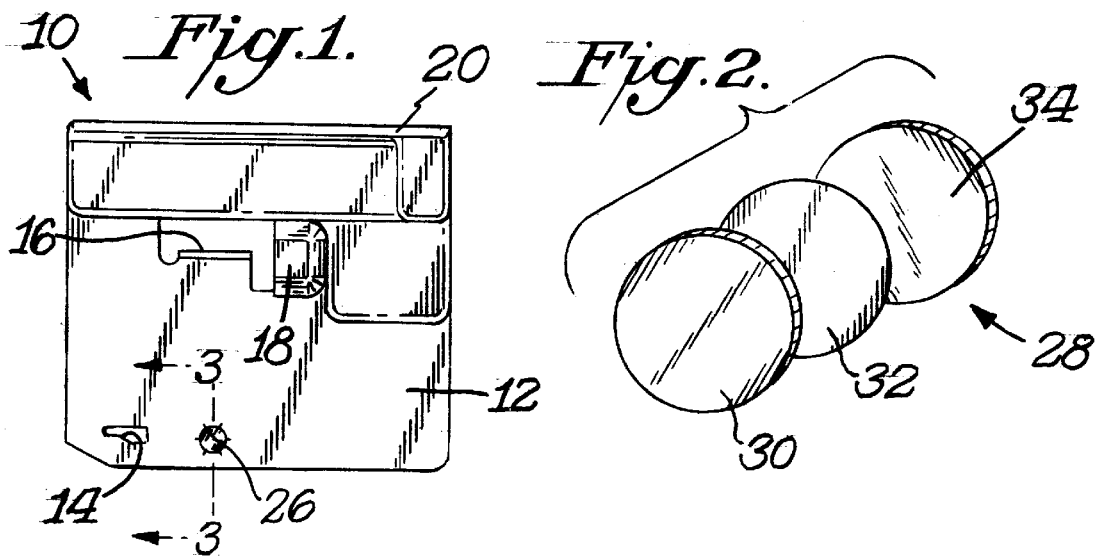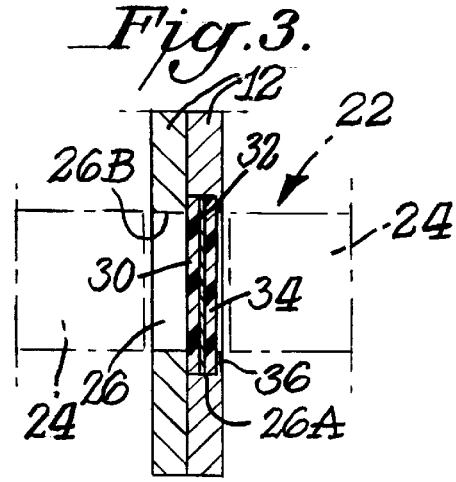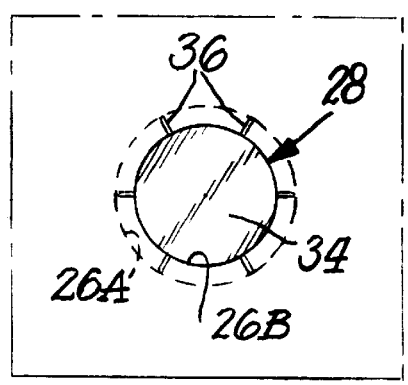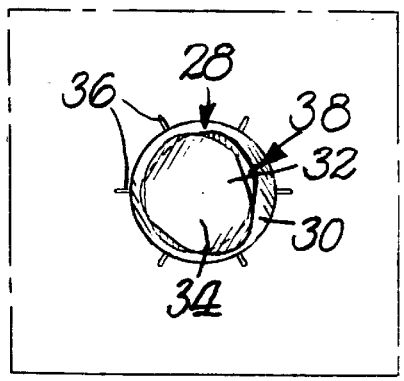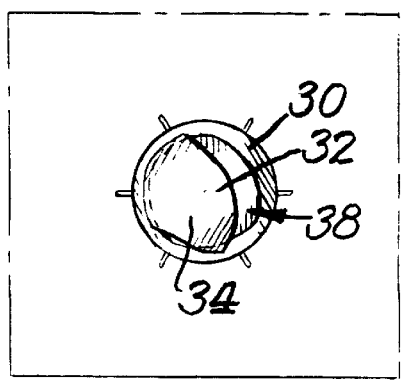

WAFER FOR USE IN SELECTIVE CONNECTING AND DISCONNECTING OF PLASTIC TUBES

BACKGROUND OF THE INVENTION

The present invention relates to wafers used for the selective connecting and disconnecting of plastic tubes such as would be used in total containment welding devices which have been described in various patents. The wafer is used in such systems as the component for heating the plastic tubes either as part of a process which disconnects a single tube and forms two tube sections for later welding of at least one of the tube sections to a tube section of a different tube. When used for the connect process the wafer applies heat to separate tube ends causing the tube ends to melt so that the melted ends could be pressed together and form a unitary tube.

Frequently the selective connecting and disconnecting of plastic tubes is performed in connection with medical techniques. Under certain circumstances it is necessary that the wafer be a single use wafer. The United States Food and Drug Administration, for example, has requirements prohibiting multiple use of devices such as wafers under certain conditions.

U.S. Pat. No. 5,525,186 discloses a particularly advantageous manner of assuring that a wafer can be used only once. As described in that patent the wafer is provided with an aperture into which a sensing material is located. During the connect/disconnect operation the wafer moves past a sensor. When the sensor detects the presence of the material in the aperture the process continues. If, however, no material is in the aperture, the absence of the material is sensed and the process is halted by deactivating the device. The particular sensing material disclosed in the '186 patent is a material which melts upon being heated. Thus, when a wafer is being used for the first time the sensing material is initially in the aperture and detected by the sensor. Subsequently, when the wafer is heated the sensing material melts and there is no longer any material in the aperture. If an attempt is made to reuse the same wafer the sensor would detect the absence of the material or the open hole or aperture.

U.S. Pat. No. 5,871,612 discloses the provision of a sensing or fuse material in the aperture wherein the sensing material has one set of light transmission characteristics prior to heating and different light transmission characteristics after the wafer is heated. Thus, a sensor would sense the proper light transmission characteristics for a wafer which has not yet been heated and would also sense the different light transmission characteristics which result after the wafer has been heated. This differs from the '186 patent in that with the Pat. '186 patent after the wafer is heated the material melts and the aperture becomes completely open. With the Pat. '612 patent, however, after the wafer is heated material still remains in the aperture but has different light transmission characteristics than it had before heating. The sensing material of the '612 patent is a two layer laminate which includes a clear base material, such as mylar, having a coating of a material having limited light transmission characteristics, such as aluminum. The material is placed in the hole or aperture of the copper wafer. When the wafer is heated the material melts thereby allowing light to pass through the fuse hole. While the fuse material of the '612 patent represents a distinct advancement in the art, there are some disadvantages which could affect its efficiency. For example, if the aluminum layer becomes too greatly scratched such as from coating wind up, slitting or punch press tooling, the scratching will cause wide variations in the optical density. Additionally, because of the two layer nature of the laminate care must be taken to properly orient the layers with respect to the sensors.

SUMMARY OF THE INVENTION

An object of this invention is to provide a wafer having fuse structure which overcomes the disadvantages of the two layer laminate disclosed in the '612 patent.

A further object of this invention is to provide such a wafer wherein the fuse material protects the meltable layer.

A still further object of this invention is to provide such a wafer wherein the fuse material is of a laminate structure whereby orientation problems are avoided.

In accordance with this invention the fuse material is a three layer laminate having a base layer or support layer on each side of the meltable layer. Preferably, the same material, such as mylar, is used for each of the outer layers. In this manner, the intermediate layer is completely shielded against the possibility of being scratched. Similarly, because of the symmetrical structure of the three layers, the orientation of the layers within the wafer aperture is not critical.

BRIEF DESCRIPTION OF THE DRAWINGS

FIG. 1 is a side elevational view of a wafer formed in accordance with this invention;

FIG. 2 is a perspective view showing the layers which comprise the fuse used in the wafer of FIG. 1;

FIG. 3 is a cross-sectional view taken through FIG. 1 along the line 3—3;

FIG. 4 is a fragmental side elevational view showing the wafer of FIG. 1 before heating; and FIGS. 5 and 6 are views similar to FIG. 4 showing the fuse material after the application of different amounts of voltage.

DETAILED DESCRIPTION

The present invention is particularly intended to provide variations of the wafers disclosed in U.S. Pat. Nos. 5,525,186 and 5,871,612, the details of which are incorporated herein by reference thereto. In general, the invention involves the use of sensing material which acts as a fuse to either permit or prevent operation of the device using the wafer as part of a connecting/disconnecting of plastic tubes.

As shown in FIG. 1 wafer 10 is in the form of a flat plate bent upon itself and thereby having a pair of opposite sides 12,12 made of a heat conductive material such as copper. Wafer 10 also includes a cut-out or notch 14 for engagement by a pawl in the home position of the wafer as described in U.S. Pat. No. 5,279,685, the details of which are incorporated herein by reference thereto. Wafer 10 also includes a wing 16 on each of its sides 12 and a scoop 18 on each of its sides generally in line with wing 16. The wings and scoops are located on the wafer at a position which would contact the melted tubes.

As also shown in FIG. 1 wafer 10 is mounted in a holder 20 the purpose of which is to mount the wafer in a carriage during the initial movement of the wafer, as described in U.S. Pat. No. 5,279,685. In operation, the wafer 10 mounted in holder 20 is moved downstream. The wafer is later detached from the holder 20. After performing its heating operation the wafer is removed from the device. During its movement wafer 10 passes through a sensing station 22 which is shown in FIG. 3. Sensing station 22 includes a sensor 24 mounted in the path of movement of aperture 26 of wafer 10. Sensor 24 would sense the amount of light or light transmission through the wafer and more particularly through aperture 26. Such sensing could be in terms, for example, of a voltage reading which would differ from the voltage reading of the main wafer material 12 and would differ from the voltage reading of a completely open hole or aperture 26. If the sensor 24 does not detect the proper voltage which is representative of the proper amount of light being transmitted through aperture 26, then the device would be inactivated. This would mean that either the wafer 10 had been previously used and no longer has sensing material of proper light transmission characteristics or that there is a manufacturing defect and the sensing material was not mounted over (in) the aperture 26.

As shown in FIGS. 2–3 the sensing material comprises a laminate or composite 28 made from a clear base material 30 such as mylar (PET). Laminate 28 also includes a further outer layer 34 which is preferably identical to outer layer 30. An intermediate layer 32 completes the laminate structure 28. Layer 32 could be a coating on one of the support layers 30 or 34 and is made of a shrinkable material having limited light transmission characteristics, such as aluminum.

The '612 patent discloses the fuse material to be mounted in such a manner that the portion of the aperture into which the fuse material is placed is a greater dimension on one side than on the other. Such mounting techniques could also be used for composite 28 herein. FIGS. 3–4 illustrate a mounting structure which includes a plurality of stakes 36 on one side 12 for holding the laminate in a mounted condition within aperture 26. Stakes 36 could be provided on each side of the laminate or preferably only on one side.

As noted in the preferred practice the stakes are provided on only one side by making use of the wafer structure being such that it is folded upon itself to create the two juxtaposed sides 12,12. Thus, the laminate 28 could be placed in aperture 26A in one of the sides of layer 12 such as the right hand side illustrated in FIG. 3. The wafer would then be folded upon itself so that the second side 12 would have an opening 26B which is smaller than opening 26A and thus extends peripherally inwardly of the outer edges of composite 28 as clearly illustrated in FIG. 3. The stakes 36 retain composite 28 in the aperture on larger aperture 26A.

Because intermediate shrinkable layer 32 is protected on both sides by outer layers 30 and 34, the problem of scratching the layer beyond acceptability is eliminated. Thus scratches that might otherwise occur from coating wind up, slitting or punch press tooling is avoided. Where outer layers 30,34 are made identical with each other, there is no problem regarding the orienting of the composite 28 in the wafer.

The present invention thereby avoids any problems that might otherwise exist with a two layer laminate because the shrinkable layer is no longer exposed and thus does not have optical density variability. The present invention avoids the need for the high degree of inspection that would be used for a two layer laminate including inspection using an optical test fixture to insure that each wafer fuse does not have excessive scratches that will falsely indicate a used wafer. Another problem attendant with the two layer fuse is that such fuse or laminate has a tendency to melt completely into a pellet that does not stick to the wafer especially when the aluminum coated side is facing the copper. With the three layer laminate 28 of this invention the above problems are alleviated. First, the aluminum layer 32 is not exposed to scratching. Second the mylar or PET should melt and stick to the copper without falling out. Third the double sided mylar will eliminate the need for orienting the aluminum side of the fuse away from the wafer. The laminate 28 is preferably a 2.8 mil aluminum coated, PET substrate, with an optical density of 1.7±0.1 cover laminated with a 2.8 mil clear PET film.

FIG. 5 illustrates the fuse material after the application of 3.67 volts. The mylar layers 30,34 are oriented mylar as a result of 2-way stretch. When heat is applied, such as at a temperature of 300° C., the orientation is released and the mylar layers begin to shrink carrying the aluminum layer with them. There is a tendency for the mylar layers to stick to certain portions of the copper wafer and shrink away from other portions. FIG. 5, for example, shows the irregular shape taken by laminate 28 after there has been some shrinkage and which leaves an open melt shrink area 38. FIG. 6 shows laminate 28 after the application of 4.8 volts. The laminate layers have shrunk a greater amount leaving a greater melt shrink area 38.

The melt shrink area 38 thus provides a path through which light can pass directly through the aperture 26. Accordingly, the passage of light results in the detection of a change in light transmission characteristics thereby indicating that the wafer has been previously heated or used.

Upon cooling the laminate 28 tends to stick to the copper wafer and thus can be discarded when the wafer is discarded. This avoids any problem of otherwise having the fuse material fall from the aperture into the machine.

Although wafer 10 has been illustrated and described as having two distinct sides 12,12 resulting from the wafer being bent upon itself, the sides may be opposite sides of a single layer plate.

What is claimed is:

1. A wafer for use in a device for selectively connecting and disconnecting plastic tubes, said wafer being in the form of a heatable flat plate having opposite sides, an aperture extending completely through said sides, a fuse located in said aperture, said fuse being made of a three layer laminate material which covers said aperture prior to a heating of said wafer and remains covering said aperture subsequent to a heating of said wafer, said fuse having its light transmission properties increased after a heating of said wafer.

2. The wafer of claim 1 wherein said laminate comprises a pair of outer layers each of which has light transmission properties, an intermediate layer having light transmission properties which differs from said light transmission properties of said outer layers, said layers shrinking upon being heated to create a melt shrink area which permits light to pass through said aperture whereby the resulting light transmission properties of said laminate is increased after said laminate has been heated.

3. The wafer of claim 2 wherein each of said outer layers is made of a transparent material.

4. The wafer of claim 2 wherein each of said outer layers is made of the same material and has the same light transmitting properties.

5. The wafer of claim 4 wherein said aperture is formed by a first hole on one side of said laminate juxtaposed to one of said outer layers, and a second aligned hole formed on an opposite side of said laminate juxtaposed to said the other of said outer layers.

6. The wafer of claim 5 wherein said first hole is of larger size than said second hole.

7. The wafer of claim 6 including a plurality of stakes at said first hole to maintain said laminate mounted in said aperture.

8. The wafer of claim 7 wherein each of said outer layers is made of mylar and said intermediate layer is made of aluminum.

9. The wafer of claim 1 wherein said aperture is formed by a first hole on one side of said laminate juxtaposed to one of said outer layers, and a second aligned hole formed on an opposite side of said laminate juxtaposed to said the other of said outer layers.

10. The wafer of claim 9 wherein said first hole is of larger size than said second hole.

11. The wafer of claim 10 including a plurality of stakes at said first hole to maintain said laminate mounted in said aperture.

12. The wafer of claim 11 wherein said sides are formed by bending said plate upon itself.

13. The wafer of claim 1 wherein said sides are formed by bending said plate upon itself.

* * * * *